United States Patent [19]

Kartinos et al.

[11] 4,339,433
[45] Jul. 13, 1982

[54] ADDITIVES FOR PERITONEAL DIALYSIS SOLUTIONS

[75] Inventors: Nicholas J. Kartinos, Park Ridge, Ill.; Terry J. McGary, 5651 E. Rocky Mountain Ave.; Karl D. Nolph, 801 Westport, both of, Columbia, Mo. 65201

[73] Assignee: Baxter Travenol Laboratories, Inc., Deerfield, Ill. ; a part interest

[21] Appl. No.: 223,638

[22] Filed: Jan. 9, 1981

[51] Int. Cl.$^3$ .................... A61K 31/74; A61K 37/00; A61K 31/70
[52] U.S. Cl. ......................... 424/78; 424/79; 424/81; 424/82; 424/177; 424/180; 128/213 A
[58] Field of Search .................. 424/78, 177, 180, 81, 424/83, 79, 82; 128/213 A; 210/645, 646

[56] References Cited

U.S. PATENT DOCUMENTS

| | | | |
|---|---|---|---|
| 2,841,578 | 7/1958 | Novak et al. | 424/180 |
| 4,133,891 | 1/1979 | Nolph | 424/295 |
| 4,235,230 | 11/1980 | Stephen et al. | 128/213 A |

OTHER PUBLICATIONS

Vercell, Chem. Abst., vol. 82, (1975), p. 144924v.
Baillie et al., Chem. Abst., vol. 90, (1979), p. 92389t.
Abouna et al., Chem. Abst., vol. 88, (1978), p. 69163q.
Rubin et al., J. of Dialysis, vol. 3, (1979), pp. 251–264.
Nolph et al., Trans. Am. Soc. Artif. Intern. Organs, 1978, pp. 162–168.

*Primary Examiner*—Sam Rosen
*Attorney, Agent, or Firm*—Paul C. Flattery; Garrettson Ellis

[57] ABSTRACT

Various polymers are added to peritoneal dialysis solutions to provide preferred alternatives to dextrose. The added polymers serve as the osmotic agents in the peritoneal dialysis solutions and provide adequate ultrafiltration.

17 Claims, 1 Drawing Figure

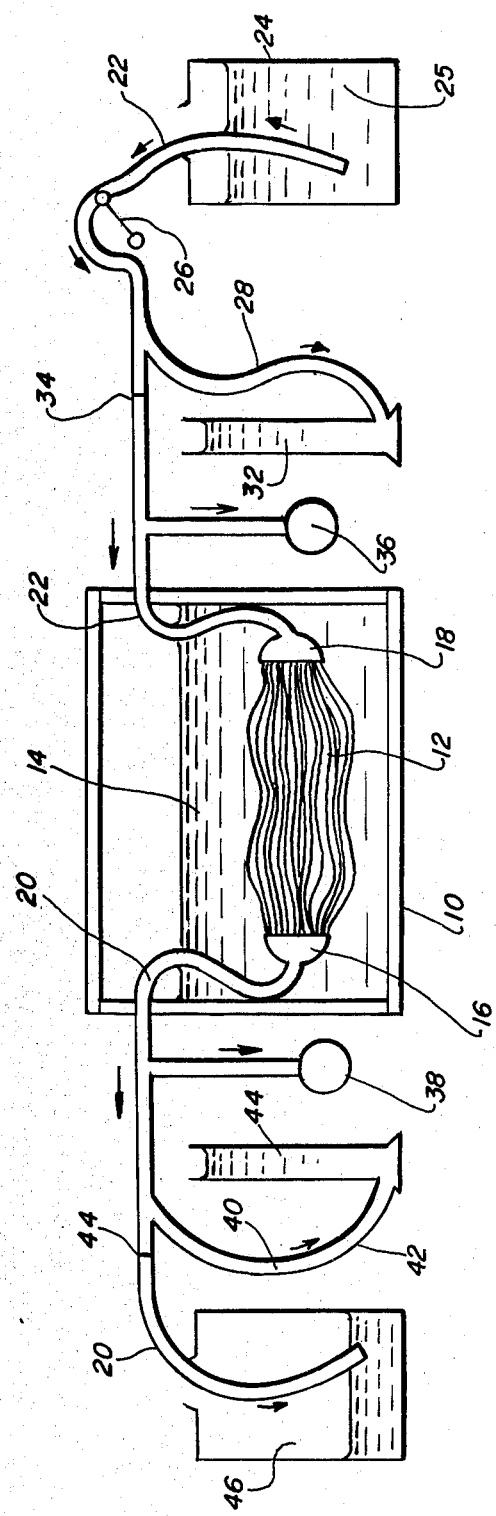

ADDITIVES FOR PERITONEAL DIALYSIS SOLUTIONS

BACKGROUND OF THE INVENTION

This invention relates to the use of polymer additives to peritoneal dialysis solutions, principally for use in the medical procedures of intermittent peritoneal dialysis (IPD) and continuous ambulatory peritoneal dialysis (CAPD).

Currently, the most widely used method of kidney dialysis for treatment of End Stage Renal Disease (ESRD) is "hemodialysis". Here, the patient's blood is cleansed by passing it through an artificial kidney in an artificial kidney dialysis machine. By the process of diffusion across a semipermeable membrane in the artificial kidney into a dialysis solution, impurities and toxins are removed from the patient's blood to thereby perform a natural function of the patient's kidneys. Water is also removed from the patient's blood, the water diffusing across the membrane of the artificial kidney into the dialysis solution; this process is called ultrafiltration.

Hemodialysis is generally required three times a week, each dialysis requiring 4 to 5 hours in a dialysis center or at home. During dialysis, the patient is "tied" to the machine by venous and arterial blood lines which convey his blood to and from the artificial kidney.

Although used less frequently than hemodialysis, a procedure known as "intermittent peritoneal dialysis" (IPD) is an accepted method for treating ESRD. In this procedure, a dialysis solution, typically containing dextrose as an osmotic agent, is infused into the patient's peritoneal cavity by means of tubing and a catheter. The peritoneum, which defines the peritoneal cavity, contains many small blood vessels and capillary beds which act as a natural semipermeable membrane. This natural membrane may be contrasted with the artificial membrane used in hemodialysis. In both cases, however, impurities, toxins, and water in the blood are removed by diffusion across a membrane—a cellulose membrane of an artificial kidney or a peritoneal membrane of a peritoneal cavity.

In intermittent peritoneal dialysis, dialysis solution remains in the patient's peritoneal cavity for a time sufficient for blood impurities and water to be removed by diffusion across the peritoneal membrane and into the dialysis solution. The impurity and water containing dialysis solution then is drained from the peritoneal cavity by means of a catheter and tubing, and a fresh supply of dialysis solution is infused. Intermittent peritoneal dialysis utilizes pumps or other auxillary equipment to which the patient is "tied" during dialysis; here also the patient must remain sedentary.

"Continuous ambulatory peritoneal dialysis" (CAPD) is another type of peritoneal dialysis which uses the peritoneum as a semipermeable membrane. The continuous procedure has the important advantage, however, of enabling the patient to be ambulatory and conduct a normal routine during dialysis. The patient is not "tied" to a machine, and he must be sedentary only for the time required to drain and infuse dialysis solution from and into the peritoneal cavity. This infusion and draining is handled by tubing and a surgically implanted, indwelling catheter in the patient's abdominal wall and in communication with his peritoneal cavity.

In a preferred method of practicing this procedure, the patient fills his peritoneal cavity with dialysis solution, typically the same dextrose-containing dialysis solution used in IPD, from a collapsible plastic container. When the container is empty, it is not disconnected from the tubing leading into the patient's peritoneal cavity. Instead, the patient simply rolls up or folds the container and tucks it into his clothing. When it is time to drain the solution from his peritoneal cavity he removes the folded container and drains directly into it. Once full, the patient then replaces the container with a container of fresh dialysis solution.

The currently used peritoneal dialysis solutions for IPD and CAPD which use dextrose as the osmotic agent have several disadvantages. A first disadvantage is that high dextrose concentration in the peritoneal dialysis solution causes dextrose to migrate through the peritoneum into the bloodstream, providing unwanted dextrose calories and possibly elevated triglyceride levels to the patient, and at the same time, reducing the osmolarity of the peritoneal dialysis solution. Unwanted dextrose is a particularly IPD or CAPD.

A second disadvantage is that dextrose in peritoneal dialysis solutions may cause the unwanted loss of amino acids and polypeptides from the blood of the patient.

Third, the pH of the dextrose-containing peritoneal dialysis solution (typically in the pH range 5.2–5.5) is not as physiologic as some physicians may desire.

It is therefore an object of the present invention to provide a peritoneal dialysis solution containing a primary osmotic agent other than dextrose that will not provide the unwanted calories and elevated triglycerides of dextrose to the patient.

It is another object of the invention to provide an osmotic agent which prevents the unwanted loss of amino acids and polypeptides from the blood of the patient.

It is a further object of the invention to provide a peritoneal dialysis solution which is in a more physiologic pH range than peritoneal dialysis solutions which use dextrose as the osmotic agent.

In accordance with this invention, polymer osmolarity-increasing agents are provided to peritoneal dialysis solutions, so that solutions of increased osmolarity and improved characteristics may be provided in which the patient does not receive unwanted dextrose into his bloodstream.

Furthermore, in accordance with this invention, peritoneal dialysis solutions may be provided in a more physiologic pH range than when dextrose is used as the osmotic agent and in which the loss of amino acids and polypeptides from the bloodstream is reduced.

Some of the preferred polymer additives to the peritoneal dialysis solutions are physiological materials related to foods, and appear to have essentially no toxicity, while at the same time providing a strong osmotic agent for the peritoneal dialysis solutions of this invention.

There is some published literature on polymer additives to peritoneal dialysis solutions. In the article by Rubin, Nolph, et al., entitled *Osmotic Ultrafiltration with Dextran Sodium Sulfate Potential for Use in Peritoneal Dialysis* from *Journal of Dialysis*, 3(263), 251–264 (1979), dextran sodium sulfate of a molecular weight of about 500,000 was evaluated in-vitro as a potential nonabsorbable osmotic agent for peritoneal dialysis. It was compared to poly (sodium acrylate) which had been shown previously to be effective in rats, but may have toxic characteristics; see *Polymer Induced Ultrafiltration In*

*Dialysis: High Osmotic Pressure Due To Impermeant Polymer Sodium,* Nolph, et al., Vol. XXIV *Trans. Am. Soc. Artif. Intern. Organs,* pp 162–168 (1978).

Dextran sodium sulfate and poly (sodium acrylate), being of high molecular weight, can reside in the peritoneal cavity of a patient without diffusing through the peritoneum into the blood stream in significant quantities. Thus, the concept of the cited articles is to use these materials, with their multiple sodium ions associated with each molecule, to increase the osmolarity of the solution for the purpose of increasing the ultrafiltration or diffusion of water through the peritoneum from the blood to the dialysis solution.

DISCLOSURE OF THE INVENTION

In accordance with this invention, a peritoneal dialysis solution is provided containing an ion concentration, to cause diffusion of water and toxins across the peritoneum after infusion of the solution into the peritoneal cavity of a patient. The peritoneal dialysis solution contains amounts of the various ions which are normally found in peritoneal dialysis solutions; for example, the following concentrations, expressed in milliequivalents per liter, as well as the ionically bound ions of the polymeric osmolarity-increasing agents of this invention:
Sodium: 132 mEq/L
Chloride: 101.5 mEq/L
Lactate: 35 mEq/L
Magnesium: 1.5 mEq/L
Calcium: 3 mEq/L The above concentrations are merely exemplary, and may be varied in accordance with patient requirements.

In accordance with this invention, sodium salts of various polymeric osmolarity-promoting agents are to be utilized as additives to peritoneal dialysis solutions. It is to be understood that while the materials used are predominantly sodium salts, they typically also include amounts of other physiological cations such as potassium, magnesium, and calcium.

There may be added to the peritoneal dialysis solution any of the following materials, which comprise predominantly sodium salts of polyionic materials, so that numerous sodium ions are associated with single polyanionic molecules. As a result of this, the sodium and other ions which are associated with the polyanions utilized in this invention cannot diffuse through the peritoneal membrane, being retained by the fixed electronegative charge of the polyanions present; the polyanions are of too high a molecular weight to diffuse through the peritoneum. Accordingly, the peritoneal dialysis solutions of this invention have high osmolarities, resulting in a substantially one way diffusion of water from the blood to the peritoneal dialysis solution in the peritoneal cavity (via the peritoneal membrane).

The polymeric osmolarity-increasing agents of this invention which may be added to the peritoneal dialysis solutions for the above purpose include the following:

(a) predominantly sodium salts of the reaction product of ethylene and a material selected from the group consisting of maleic acid and maleic anhydride;

(b) predominantly sodium salts of carboxymethylpolysaccharides;

(c) predominantly sodium salts of carboxymethylpolyvinyl alcohol;

(d) predominantly sodium salts of polypeptides and proteins containing at least 10 mole percent of peptide units selected from the group consisting of aspartic acid, glutamic acid, and combinations thereof, having pendant carboxyl groups;

(e) predominantly sodium salts of esters of polyvinyl alcohol with acids selected from the group consisting of sulfuric acid, phosphoric acid, polycarboxylic acids, and haloalkyl carboxylic acids, having pendant carboxyl groups;

(f) predominantly sodium salts of the reaction product between (1) polypeptides and proteins having pendant amine groups, and (2) acids selected from the group consisting of dicarboxylic acids and anhydrides thereof, haloaliphatic carboxylic acids, and haloalkenic carboxylic acids; preferably 10 to 50 or more mole percent of the peptide units present have pendant amine groups for reaction with the acids specified;

(g) predominantly sodium salts of polyesters, having pendant carboxyl groups, comprising hydroxypolycarboxylic acids;

(h) predominantly sodium salts of poly (methylvinyl ether—maleic acid) having pendant carboxyl groups;

(i) predominantly sodium salts of the reaction product of (1) an amino acid and (2) acid halides of dicarboxylic acids, to yield a polyamide polymer chain having pendant carboxyl groups; and (j) predominantly sodium salts of dextran sulfate having a molecular weight of 2000 to 120,000.

As one particular species of item (f) above, a gelatin may be reacted with polycarboxylic acids or anhydrides thereof to provide a polyanionic protein material having pendant carboxyl groups. Preferably the dicarboxylic acid used may be a dicarboxylic acid such as succinic acid, maleic acid, or tartaric acid, among others.

It is contemplated that the polymeric materials used in this invention are usually not saturated sodium salts, but only partial salts, with the anionic sites of the polymeric osmolarity-increasing agents outnumbering the metallic cations available for association with the anionic sites, so that the pH of the peritoneal dialysis solution is not excessively high, generally not in excess of pH 7.5, and typically in the pH range 6.8–7.2. Also typically, the anionic sites not ionically bonded to a metal cation are acid sites with acidic hydrogen. If desired, the pH of the peritoneal dialysis solution utilizing the agents of this invention may be reduced by the addition of the hydrochloric acid, acetic acid, or the like.

Specifically, referring to material described under (a) above, ethylene-maleic acid copolymer resins and lower molecular weight reaction products, are well known, and are commercially available, particularly in the ethylene-maleic acid anhydride form. In alkaline solution, the ethylene-maleic anhydride copolymers tend to hydrolyze and to form sodium salts, although preferably partial sodium salts (which are not saturated with sodium) are preferred for control of the pH, as stated before.

Specifically, referring to Section (a) above, 12.6 grams of ethylene-maleic anhydride resin (EMA 21, sold by Monsanto of St. Louis, Mo.) was suspended in 100 ml. of distilled water. Thereafter, 8 grams, or 0.2 mole, of sodium hydroxide pellets were added. An exothermic reaction ensued, and the ethylene-maleic anhydride polymer gradually dissolved.

After standing at room temperature for a period, the strongly alkaline solution was diluted with 1 normal hydrochloric acid to a pH of 6.8. The resulting solution was diluted with distilled water to 750 ml., and filtered, and thereafter diluted further to 1 liter with distilled water.

The resulting solution was found to have an osmolarity of 180.8 milliosmoles per kilogram, with approximately 182 milliequivalents of sodium being present.

When the polymeric material prepared by the technique described immediately above is added to conventional, dextrose-free, peritoneal dialysis solution, the osmolarity of the solution can be raised to cause acceptable rates of ultrafiltration to take place in peritoneal dialysis procedures without the migration of detectable amounts of the sodium salt of the ethylene-maleic acid copolymer into the blood.

Referring to Section (b) above, many different sodium salts of carboxymethylpolysaccharides may be used. It is particularly preferred to use appropriate sodium salts of carboxymethylstarch or carboxymethyldextran. Alternatively, other polysaccharide salts of sodium may be used, for example, an oligosaccharide or a sodium-potassium-magnesium-calcium equilibrated salt derived from gum arabic, in which most of the naturally occurring other ions in the gum arabic are replaced with sodium or hydroxyl groups by means of washing with a sodium chloride solution, for example, containing minor amounts of the other ions mentioned.

Referring to Section (c) above, polyvinyl alcohols which are commercially available materials, can be conventionally modified by a process similar to the manufacturing process for carboxymethylcellulose to carry pendant carboxymethyl groups which, in turn, form salts with sodium and related metal ions to form yet another class of compounds usable as the polyionic osmolarity-increasing agents of this invention.

Referring to Section (d) above, polypeptides and proteins, which contain at least about 10 mole percent of peptide units (and preferably up to 100 percent) which are either aspartic acid, glutamic acid, or combinations thereof, can be synthesized having many pendant carboxyl groups from these two amino acids. These carboxyl groups, in turn, are reacted to form predominantly sodium salts which are polyanionic, and which may be used in accordance with this invention without diffusion in significant quantities through the peritoneum.

Referring to Section (e) above, polyvinyl alcohol may be esterified with polyfunctional acids such as sulfuric acids, phosphoric acid, or polycarboxylic acids such as succinic acid, glutaric acid, adipic acid, tartaric acid, and the like. Also, haloalkylcarboxylic acids may be reacted with polyvinyl alcohol to provide pendant carboxyl groups, for example, chloroacetic acid, iodohexanoic acid, or bromopropionic acid, which then can form predominantly polysodium salts.

Referring to Section (f) above, predominantly sodium salts of the reaction products between (1) polypeptides and proteins containing a substantial amount (preferably at least 10 mole percent) of peptide units having pendant amine groups may be reacted with (2) a molar excess of dicarboxylic acids or their anhydrides, haloaliphatic carboxylic acids, and haloalkenic carboxylic acids.

Basically, the polymer in this instance is a protein or polypeptide material in which a substantial amount of the amino acid precursors have more than one amine group, so that the resulting polypeptide or protein has a substantial amount of pendant amine groups. These pendant amine groups may, in turn, be reacted with dicarboxylic acids or their anhydrides, to form pendant carboxyl group structures off of the protein or polypeptide polymer backbone. Examples of available polycarboxylic acids have been cited above.

Alternatively, haloaliphatic carboxylic acids or haloalkenic carboxylic acids may react with the pendant amine groups of the proteins and polypeptides contemplated for use herein, under the well known conditions for the reaction of a halialkyl linkage with an amine, for providing by another means pendant carboxylic acids to the polymer chain.

Haloaliphatic carboxylic acids are previously described may be used, while suitable haloalkenic carboxylic acids may also be used.

Referring to Section (g), predominantly sodium salts of polyesters which are characterized by having pendant carboxyl groups capable of forming the sodium salts may be used. Specifically, the contemplated polyesters may include homopolymers of hydroxydicarboxylic acids, or which optionally may be co-polymerized with polyesters of dicarboxylic acids such as succinic acid, or adipic acid, coesterified with a diol material such as polyethylenediol or the like.

Hydroxydicarboxylic acids contain two carboxyl groups and ony hydroxy group, for example, and thus are capable of spontaneously forming a polyester either as a homopolymer, or else in combination with other materials such as those previously mentioned. Examples of hydroxydicarboxylic acids include maleic acid, tartaric acid, and citric acid, which are all naturally occurring acids. Other acids such as 2-hydroxyadipic acid and similar materials are also usable to form polyester homopolymers or copolymers having pendant carboxyl groups, or other materials as described above. This polymerization reaction can take place under known conditions, for example, heating in vacuo at 130° C. in the presence of 50 to 500 ppm of stannous octoate.

Referring to Section (h) above, copolymers of methylvinyl ether and unsaturated carboxylic acids such as maleic acid are known, having pendant carboxyl groups which may take the predominantly sodium salt form for use in this invention.

Referring to Section (i) above, the acyl halides of dicarboxylic acids such as oxalyl chloride or the diacid bromide or succinic acid can react with an amino acid such as glycine to yield a polyamide having pendant carboxylic groups. This may be reacted to form a polyionic predominantly sodium salt, for use as described in this invention.

Referring to Section (j) above, in the article of Nolph et al. in Volume 24, Transactions ASAIO (1978) pp. 162, at page 166, the use of dextran sulfate as an ultrafiltration inducing agent is disclosed. However, it is indicated in accordance with this invention that the predominantly sodium salts of dextran sulfate having molecular weights of preferably 2,000 to 120,000 exhibit substantially improved ultrafiltration-inducing reaction in peritoneal dialysis solutions, when compared with higher molecular weight dextran sulfate materials, for example molecular weights on the order of 500,000 which were contemplated when the Nolph, et al. 1978 article was written.

The examples below are offered in the spirit of illustrating the invention of this application, rather than limiting the scope of the invention, which is as defined in the claims below:

EXAMPLE I

As in vitro evaluation of polyanionic compounds as osmotic agents was performed under simulated peritoneal dialysis conditions.

Three polyanionic materials were utilized in the study, and were evaluated for their ability to produce osmotic ultrafiltration.

The three polyanionic materials tested were (1) dextran sodium sulfate, (2) a gelatin reacted with a succinic anhydride or succinic acid to form a high molecular weight protein having pendant carboxyl groups (sold by B. Braun Melsungen A. G. under the trademark NEO-PLASMAGEL), and (3) sodium poly (ethylene maleate).

FIG. 1 is a schematic view of the experimental setup used for testing the polyanionic materials of this example.

Referring to FIG. 1, a plexiglass container 10 contains a 0.6 square meter, commercially available hollow fiber dialyzer 12 with the outer casing removed, is submerged in a 2 liter pool of dialysis solution 14, and placed in a warming bath at 37° C. The manifold ends 16, 18 of the fiber dialyzer 12 are each connected to tubing 20, 22. Perfusate 25 used is stored in container 24 and passed by means of a roller pump 26 through tubing 22 and through the interiors of the hollow fibers of hollow fiber dialyzer 12. Branch line 28, controlled by clamp 30, communicates with a graduated cylinder 32, so that flow rates can be measured simply by opening clamp 30 for a timed period, while closing clamp 34 of tubing 22.

The inlet flow of perfusate was set at 100 ml. per minute and checked at the beginning and end of each study period. Connected pressure gauges 36, 38, adjacent the inlet and outlet to dialyzer 12 are also provided as shown.

Branch line 40, controlled by clamp 42, leads to graduated cylinder 44 for monitoring of the outlet flow through tubing 20 by appropriate manipulation of clamp 42, controlling flow through line 40, and clamp 46, controlling flow through line 20, so that liquid can flow into graduated cylinder 44 for a timed period, to calculate flow rates.

Finally, tubing 20 communicates with receptacle 48 for receiving the output of the system.

To assure the integrity of the fibers of dialyzer 12 through the experimental procedure, control studies were performed at the beginning and end of each experimental series. During these studies a deionized water perfusate 25 and a distilled water dialysate 14 (dialysate 14 simulating a peritoneal dialysis solution) were used under minimal transmembrane hydrostatic pressure conditions, to determine ultrafiltration rates. Accordingly, during the studies of the effect of the polyanionic materials of this invention, corrections could be made for portions of measured ultrafiltration rates created by pressure differentials across the capillary fibers of the dialyzer 12. Also, these controlled studies assure that the hydraulic ultrafiltration characteristics of the dialyzer have not been altered by duration of use, or by physical manipulation of the dialyzer fibers.

After the initial preparation, solutions of the polyanionic materials utilized herein were dialyzed in conventional apparatus to remove small polymer fragments and free electrolytes. The polyanionic materials were dialyzed one to three times, single pass, against deionized water in an intact hollow fiber 0.6 square meter artificial kidney of a commercially available type.

With respect to the dextran sodium sulfate utilized herein, it was obtained from Pharmachem of Bethlehem, Pa. and had an average molecular weight of about 5,000. Two concentrations of the dextran sodium sulfate were utilized for the experiment: a 7.5 percent by weight solution which, after predialysis of 6 liters of such solution, yielded a sodium concentration on the polymer of 295 mEq/L and a 10 percent solution of the dextran sodium sulfate.

Four liters of the 10 percent dextran sulphate solution yielded a sodium concentration on the polymer of 373 mEq/L, while a separate lot of 6 liters of the 10 percent solution was prepared in distilled water, which, after predialysis yielded a sodium concentration of 390 mEq/L.

With respect to the succinylated gelatin, it had an average molecular weight of 35,000 and was obtained from B. Braun Melsungen AG. in Germany. This material was used with a single predialysis, and after predialysis had a sodium concentration of 60 mEq/L.

With respect to the sodium poly (ethylene maleate), it had an average molecular weight of about 8,000. The anhydride form was obtained from Monsanto Chemical Company of St. Louis, Mo. A 10 percent solution of the sodium poly (ethylene maleate) was prepared in 3 liters of distilled water with the hydrolysis of the anhydride form being completed by adding 190.48 grams of sodium hydroxide pellets. An exothermic reaction took place and the reaction was allowed to stir overnight at ambient temperatures. Approximately 350 ml. of 6 N hydrochloric acid was added, for back titration of a desired pH of 7.0. After predialysis, the solution yielded a volume of 4 liters, and a polymer sodium concentration of 471 mEq/L.

At the beginning of each study, single pass perfusion through dialyzer 12 was established at an inlet flow rate of 100 ml/min. Then, the chamber 10, filled with water during the start-up period, was drained rapidly and rinsed. The experimental dialysate solution 14 was then added over 25 to 30 seconds to chamber 10. Ten ml. aliquot samples of dialysate 14 and samples of the perfusate inflow and outflow were obtained during each two-hour exchange period at 3, 5, 10, 20, 30, 45, 60, 90 and 120 minutes. The ultrafiltration was evaluated at each sample interval by flow diversion into graduated cylinder 44, and subtracting this flow rate from the inlet flow rate as measured by diversion of flow into graduated cylinder 32, with the flow rate setting of roller pump 26 being constant. Thus ultrafiltration could be calculated.

Also, the dialysate volume change in container 10 from the beginning to the end of each experimental exchange was used as a check calculation of the ultrafiltration rate.

The polymer sodium contents described above were calculated by the total sodium present, minus the chloride concentration.

The inlet pressure reported on pressure manometer 36 during the studies was generally kept at no more than 25 ml. of mercury for a low inlet pressure, while the outlet pressure measured at pressure manometer 38 was generally maintained below 1 ml. of mercury, to minimize hydrostatic effects on ultrafiltration.

While much data of various kinds was obtained with the above study system, the data below represents what is believed to be the most pertinent data relative to the invention of this application.

In studies where the polyanionic agents of this invention were placed in the dialysate 14 and dialyzed against water as the perfusate 25, the ultrafiltration results were as shown in Table I below:

TABLE I

| Polymer | Polymer Sodium Content (mEq/L) | Percent of Polymer in Solution (wt-vol) | Average Ultra-filtration ml. per minute |
|---|---|---|---|
| Dextran Sodium Sulfate | 390 | 10 | 11.67 |
| Ethylene Maleate | 471 | 10 | 15.08 |
| Succinylated Gelatin | 60 | 3 | 2.83 |

Accordingly, it can be seen that substantial ultrafiltration of perfusate 25 can take place into dialysate 14 in the presence of the polyanionic materials of this invention.

EXAMPLE II

The experiment of Example I was repeated, using 140 mEq/L sodium chloride solution as perfusate 25, and solutions of the polyanionic agents of this invention in distilled water as dialysate 14. From the data of Table II, it can be seen that the ultrafiltration is suppressed relative to Example I but not eliminated by the presence of sodium chloride in perfusate 25. Also, as expected, sodium chloride from the perfusate solution passes across the membrane into the dialysate at the average rate indicated during the two-hour procedure.

TABLE II

| Polymer | Polymer Sodium Content (mEq/L) | Percent of Polymer in Solution (wt-vol%) | Average Ultra-filtration ml. per minute | Average Sodium Clearance of Sodium (ml./min.) |
|---|---|---|---|---|
| Dextran Sulfate | 294 | 7.5 | 3.47 | 11.30 |
| Dextran Sulfate | 373 | 10.0 | 5.46 | 9.79 |
| Ethylene Maleate | 471 | 10.0 | 6.09 | 6.59 |

EXAMPLE III

The studies of Examples I and II were continued by other runs, with the saline perfusate 25 of Example II being dialyzed against various polyanionic polymers in accordance with this invention, also containing free sodium chloride in solution. The dextran sodium sulfate solutions in Table III below were in 80 mEq/L free sodium chloride solution. The ethylene maleate solution contained 28 mEq/L of free sodium chloride, while the succinylated gelatin contained 80 mEq/L of free sodium chloride in solution.

TABLE III

| Polymer | Polymer Sodium Content (mEq/L) | Percent of Polymer in Solution (wt-vol%) | Average Ultra-filtration ml. per minute | Average Sodium Clearance of Sodium (ml./min.) |
|---|---|---|---|---|
| Dextran Sodium Sulfate | 294 | 7.5 | 3.9 | 2.5 |
| Dextran Sodium Sulfate | 373 | 10.0 | 5.6 | 0.3 |
| Dextran Sodium Sulfate | 390 | 10.0 | 5.9 | 0.5 |
| Ethylene Maleate | 471 | 10.0 | 5.0 | 4.9 |
| Succinylated Gelatin | 60 | 3.0 | 0.8 | 2.0 |

The ultrafiltration curves obtained by the experiments in all cases tended to exhibit a decrease over the two-hour period of each of the experiments of Examples I to III, the decrease being to a final ultrafiltration value which was generally no less than and usually more than one-half the initial ultrafiltration value.

EXAMPLE IV

A dextran sodium sulfate having an average molecular weight of 40,000 was dissolved in water to a concentration to provide 490 mEq/L of sodium, and used in the experiment of the previous examples as the dialysate 14.

The perfusate 25 was a saline solution similar to that of Example II.

Upon a two-hour dialysis procedure similar to those previously described, the following ultrafiltration rates through dialyzer fibers 12 from the perfusate 25 to the dialysate 14 was observed, expressed as a function of time in Table IV below:

TABLE IV

| Time | Ultrafiltration ml./min. | Clearance of Sodium ml./min. |
|---|---|---|
| 10 minutes | 8.4 | 13.2 |
| 30 minutes | 7.7 | 7.5 |
| 60 minutes | 6.0 | 6.6 |
| 120 minutes | 5.5 | 1.6 |

EXAMPLE V

The experiment of Example IV was repeated utilizing a dextran sodium sulfate of an average molecular weight of about 40,000 in solution to provide 590 mEq/L of sodium, and dialyzed against saline solution. The results are as shown in Table V below:

TABLE V

| Time | Ultrafiltration ml/min. | Clearance of Sodium ml./min. |
|---|---|---|
| 10 minutes | 11.0 | 11.4 |
| 30 minutes | 10.2 | 5.8 |
| 60 minutes | 8.6 | 2.0 |
| 120 minutes | 6.8 | 1.3 |

Note in this instance the clear increase in ultrafiltration over sodium clearance, showing how more water may be removed from perfusate 25 than sodium, to cause a net increase in the sodium concentration of the perfusate.

The experimental results indicate that the amount of ultrafiltration which takes place in the experimental systems described above is generally proportional to the amount of polymer sodium in the anionic polymers utilized in the experiments above. This relation holds substantially true, at least as an approximation, irrespective of whether the perfusate 25 is pure water or a saline solution.

Also, the experiments show that the ultrafiltration of the systems examined in the experiments above are generally proportional to the mean transmembrane osmolarity of the perfusate 25 on one side of the membrane fibers 12, and the dialysate 14 on the other side.

Accordingly, the polymeric additives disclosed in this invention provide osmotic agents that, when added to peritoneal dialysis solutions as an alternative to the currently used osmotic agent dextrose, provide adequate ultrafiltration without the disadvantages of dextrose.

The above has been offered for illustrative purposes only, and is not intended to limit the invention of this application, which is as defined in the claims below.

That which is claimed is:

1. In a peritoneal dialysis solution containing ion concentration to permit diffusion across the peritoneum after infusion of the solution into the peritoneal cavity of a patient, the improvement comprising:
said solution containing a polyionic osmolarity-increasing agent which is of a molecular weight sufficient to essentially prevent diffusion of said agent across the peritoneum, said agent being selected from the group consisting of the predominantly sodium salts of:
(a) ethylene-maleic acid copolymer resins;
(b) carboxymethylpolysaccharides;
(c) carboxymethylpolyvinyl alcohol;
(d) polypeptides and proteins containing at least 10 mole percent of peptide units selected from the group consisting of aspartic acid, glutamic acid, and combinations thereof, having pendant carboxyl groups;
(e) esters of polyvinyl alcohol with acids selected from the group consisting of sulfuric acid, phosphoric acid, polycarboxylic acids, and haloalkyl carboxylic acids; having pendant carboxyl groups;
(f) the reaction product between (1) polypeptides and proteins having pendant amine groups and (2) acids selected from the group consisting of dicarboxylic acids and anhydrides thereof, haloaliphatic carboxylic acids, and haloalkenic carboxylic acids;
(g) polyesters having pendant carboxyl groups, comprising hydroxylpolycarboxylic acids;
(h) poly(methylvinyl ether—maleic acid) having pendant carboxyl groups;
(i) the reaction product of (1) an amino acid and (2) acid halides of dicarboxylic acids, to yield a polyamide polymer chain having pendant carboxyl groups; and
(j) predominantly sodium salts of dextran sulfate having a molecular weight of 2,000 to 120,000.

2. The peritoneal dialysis solution of claim 1 in which said osmolarity-increasing agent is a mixed salt including sodium, potassium, magnesium, and calcium ions.

3. In a peritoneal dialysis solution containing ion concentration to permit safe diffusion exchange across the peritoneum after diffusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of an ethylene-maleic acid copolymer resin.

4. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of a carboxymethylpolysaccharide.

5. The peritoneal dialysis solution of claim 4 in which said polysaccharide is an oligosaccharide.

6. The peritoneal dialysis solution of claim 4 in which said polysaccharide is a carboxymethyl starch.

7. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of carboxymethylpolyvinyl alcohol.

8. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of polypeptides and proteins containing at least ten mole percent of peptide units selected from the group consisting of aspartic acid, glutamic acid, and combinations thereof, having pendant carboxyl groups.

9. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of esters of polyvinyl alcohol with acids selected from the group consisting of sulfuric acid, phosphoric acid, polycarboxylic acids, and haloalkyl carboxylic acids, having pendant carboxyl groups.

10. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of the reaction product between (1) polypeptides and proteins having pendant amine groups and (2) acids selected from the group consisting of dicarboxylic acids and anhydrides thereof, haloaliphatic carboxylic acids, and haloalkenic carboxylic acids.

11. In a peritoneal dialysis solution containing an ion concentration to permit safe diffusion exchange across the peritoneum after infusion into the peritoneal cavity of a patient, the improvement comprising:
said solution containing a polyionic osmolarity-increasing agent which is of a molecular weight sufficient to essentially prevent diffusion of said agent across the peritoneum, said agent being a predominantly sodium salt of polyesters having pendant carboxyl groups, comprising hydroxypolycarboxylic acids.

12. In a peritoneal dialysis solution containing an ion concentration to permit safe diffusion exchange across the peritoneum after infusion into the peritoneal cavity of a patient, the improvement comprising:

said solution containing a polyionic osmolarity-increasing agent which is of a molecular weight sufficient to essentially prevent diffusion of said agent across the peritoneum, said agent being a predominantly sodium salt of poly (methylvinyl ether-maleic acid) having pendant carboxyl groups.

13. In a peritoneal dialysis solution containing a physiological ion concentration to permit safe diffusion exchange across the peritoneum after infusion into the peritoneal cavity of a patient, the improvement comprising:

said solution containing a polyionic osmolarity-increasing agent which is of a molecular weight sufficient to essentially prevent diffusion of said agent across the peritoneum, said agent being a predominantly sodium salt of the reaction product of (1) an amino acid and (2) acid halides of dicarboxylic acids, to yield a polyamide polymer chain having pendant carboxyl groups.

14. In a peritoneal dialysis solution containing an ion concentration to permit safe diffusion exchange across the peritoneum after infusion into the peritoneal cavity of a patient, the improvement comprising:

said solution containing a polyionic osmolarity-increasing agent which is of a molecular weight sufficient to essentially prevent diffusion of said agent across the peritoneum, said agent being a predominantly sodium salt of dextran sulfate having a molecular weight of 2,000 to 120,000.

15. In a peritoneal dialysis solution containing an ion concentration to permit safe diffusion exchange across the peritoneum after infusion into the peritoneal cavity of a patient, the improvement comprising:

said solution containing a polyionic osmolarity-increasing agent which is of a molecular weight sufficient to essentially prevent diffusion of said agent across the peritoneum, said agent being a predominantly sodium salt of the reaction product of a gelatin and a material selected from the group consisting of dicarboxylic acids and anhydrides thereof, said reaction product comprising a polyionic protein material having pendant carboxyl groups.

16. The peritoneal dialysis solution of claim 15 in which said dicarboxylic acids are selected from the group consisting of succinic acid, maleic acid, and tartaric acid.

17. The peritoneal dialysis solution of claim 15 in which said dicarboxylic acid is succinic acid.

* * * * *